(12) United States Patent
Chiarugi et al.

(10) Patent No.: US 8,752,411 B2
(45) Date of Patent: Jun. 17, 2014

(54) DEVICE FOR DETECTING VOLATILE SUBSTANCES, APPARATUS USING THE DEVICE AND RELATED OPERATIVE METHOD

(75) Inventors: Luca Chiarugi, Genoa (IT); Gian Paolo Tonini, Genoa (IT); Tiziana Ruzzon, Genoa (IT)

(73) Assignees: IRCCS Azienda Ospedaliera Universitaria San Martino—IST—Instituto Nazionale per la Ricerca sul Cancro (IT); Omega S.R.L. (IT)

( * ) Notice: Subject to any disclaimer, the term of this patent is extended or adjusted under 35 U.S.C. 154(b) by 0 days.

(21) Appl. No.: 13/504,939

(22) PCT Filed: Nov. 10, 2010

(86) PCT No.: PCT/IT2010/000448
§ 371 (c)(1),
(2), (4) Date: Jun. 27, 2012

(87) PCT Pub. No.: WO2011/058592
PCT Pub. Date: May 19, 2011

(65) Prior Publication Data
US 2012/0266654 A1    Oct. 25, 2012

(30) Foreign Application Priority Data
Nov. 11, 2009 (IT) .............................. RM2009A0581

(51) Int. Cl.
*G01N 30/02* (2006.01)
(52) U.S. Cl.
USPC ......... 73/19.1; 73/19.12; 73/31.05; 73/31.07; 73/863.12

(58) Field of Classification Search
CPC ............ G01N 1/2226; G01N 33/0047; G01N 2001/002; G01N 33/0331; G01N 33/0021; G01N 33/68
USPC ............. 73/19.1, 19.12, 31.07, 31.05, 863.12
See application file for complete search history.

(56) References Cited

U.S. PATENT DOCUMENTS

| 4,541,268 A | 9/1985 | Odernheimer |
| 5,331,845 A * | 7/1994 | Bals et al. .................... 73/61.43 |

(Continued)

FOREIGN PATENT DOCUMENTS

| EP | 1471343 | 10/2004 |
| EP | 1584912 | 10/2005 |

OTHER PUBLICATIONS

PCT Search Report of International Application PCT/IT2010/000448 filed Nov. 10, 2010 in the name of Istituto Nazionale Per La Ricerca Sul Cancro, Mail Date: Jan. 19, 2011.

(Continued)

*Primary Examiner* — Hezron E Williams
*Assistant Examiner* — Alexander Mercado
(74) *Attorney, Agent, or Firm* — Steinfl & Bruno LLP

(57) ABSTRACT

A device for detecting volatile substances has a containment box with at least one inlet opening for introduction of gas flow, one or more outlet openings of the gas flow, at least one analysis opening, one or more detection sensors arranged in the containment box, and at least one probe insertable in the containment box through at least one analysis opening. When the probe is initially treated by a sample of a substance to be examined and is inserted in the containment box, the gas flow uniformly carries the volatile substances from the sample to one or more sensors. A detection apparatus and a detection method for volatile substances are also described.

20 Claims, 7 Drawing Sheets

(56) References Cited

U.S. PATENT DOCUMENTS

| | | | |
|---|---|---|---|
| 5,741,984 A | | 4/1998 | Danylewych-May et al. |
| 5,773,713 A | * | 6/1998 | Barber et al. ................ 73/61.41 |
| 6,125,687 A | * | 10/2000 | McClelland et al. ........ 73/19.01 |
| 6,277,329 B1 | * | 8/2001 | Evans ............................ 422/80 |
| 6,978,657 B1 | * | 12/2005 | Baumann et al. ............ 73/28.04 |
| 7,963,146 B2 | * | 6/2011 | Petinarides .................. 73/31.02 |
| 2001/0016357 A1 | * | 8/2001 | Ledig ............................ 436/177 |
| 2002/0124631 A1 | * | 9/2002 | Sunshine et al. ................ 73/23.2 |
| 2010/0077828 A1 | * | 4/2010 | Herz et al. .................... 73/1.03 |
| 2010/0251802 A1 | * | 10/2010 | Patel et al. .................... 73/19.1 |

OTHER PUBLICATIONS

PCT Written Opinion of International Application PCT/IT2010/000448 filed Nov. 10, 2010 in the name of Istituto Nazionale Per La Ricerca Sul Cancro, Mail Date: Jan. 19, 2011.

PCT International Preliminary Report on Patentability of International Application PCT/IT2010/000448 filed Nov. 10, 2010 in the name of Istituto Nazionale Per La Ricerca Sul Cancro, Mail Date: Oct. 21, 2011.

* cited by examiner

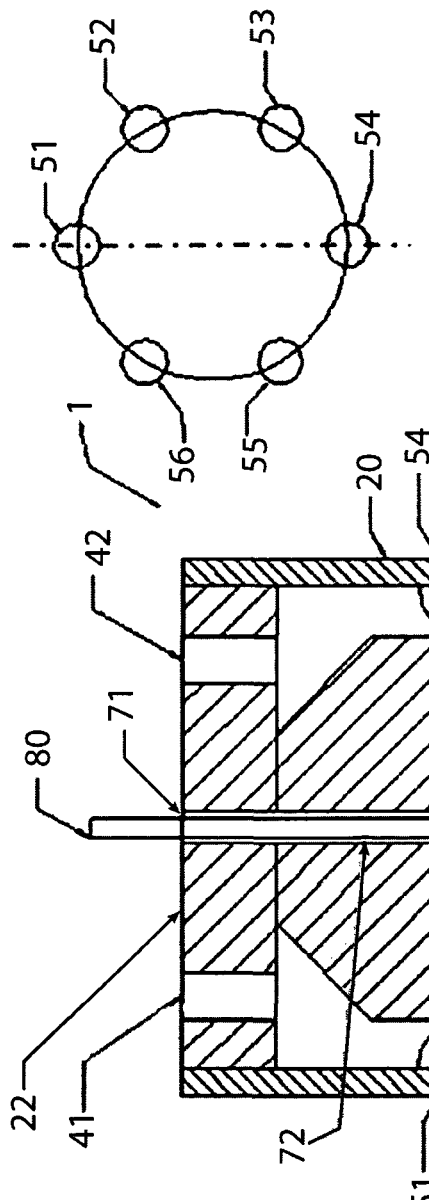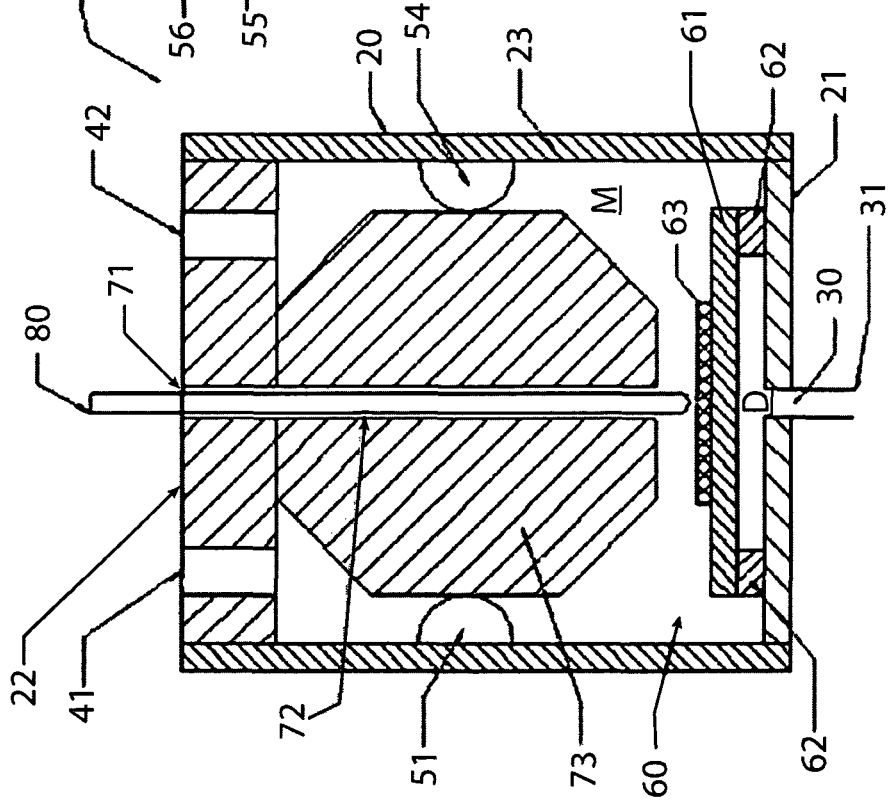
Fig. 1
Fig. 2

| CAMPIONE | mg/500 ul urina |
|---|---|
| 1 AOV | 0,5 |
| 2 AOV | 0,2 |
| 3 AOV | 0,1 |
| 4 AOV | 0,01 |
| 5 AOV | 0,001 |
| 6 AOV | 0,0001 |
| 7 AOV | 0,00005 |
| 1 AVM | 0,5 |
| 2 AVM | 0,2 |
| 3 AVM | 0,1 |
| 4 AVM | 0,01 |
| 5 AVM | 0,001 |
| 6 AVM | 0,0001 |
| 7 AVM | 0,00005 |
| 1 MIX AOV+AVM | 0,5 AOV + 0,5 AVM |
| 2 MIX AOV+AVM | 0,2 AOV + 0,2 AVM |
| 3 MIX AOV+AVM | 0,1 AOV + 0,1 AVM |
| 4 MIX AOV+AVM | 0,01 AOV + 0,01 AVM |
| 5 MIX AOV+AVM | 0,001 AOV + 0,001 AVM |
| 6 MIX AOV+AVM | 0,0001 AOV + 0,0001 AVM |
| 7 MIX AOV+AVM | 0,00005 AOV + 0,00005 AVM |

ALLEGATO NUMERO 3 SOLUZIONI TESTATI

*Fig. 5*

DEVICE FOR DETECTING VOLATILE SUBSTANCES, APPARATUS USING THE DEVICE AND RELATED OPERATIVE METHOD

CROSS REFERENCE TO RELATED APPLICATIONS

The present application is the US national stage of international application PCT/IT2010/000448 filed on Nov. 10, 2010 which, in turn, claims priority to Italian Patent Application RM2009A000581 filed on Nov. 11, 2009.

FIELD

The present invention relates to a device for detecting volatile substances, to an apparatus using said device and to the relevant operative method.

More specifically, the invention concerns a device that can sample and analyze substances that are present within liquid and/or solid samples in an amount in the order of some micro liters, to detect volatile portions. The device can be easily employed and ensures high operation stability.

The present disclosure will address detection of volatile substances contained in urine, and particularly detection of markers useful to diagnosis of neuroblastoma and to monitor course of disease. The device of the present disclosure should not be considered as limited to such specific use.

BACKGROUND

At present, it is necessary to detect clinical-biological parameters in the diagnosis of neuroblastoma, which include the determination of homovanillic and vanilmandelic acid within patient urine. Presently, examination of the acids within urines is carried out with specialized centers by HPLC (High Pressure Liquid Chromatography), i.e. an expensive and difficult analysis.

Examples of the device for measurement of volatile substances are found in patent applications EP 1584912, U.S. Pat. No. 4,541,268 and EP 1417343.

The patent application U.S. Pat. No. 5,741,984 describes an apparatus for the measurement of volatile substances according to the preamble of claim 1.

SUMMARY

In view of the above, it is an object of the present invention to suggest a device that can carry out measurements of volatile substances with a high stability, quickly, and at very low costs.

Another object of the present invention is to suggest a device for detecting and measuring volatile substances, that can be easily used even by those not skilled in the art.

Therefore, the specific objective of the present invention is that of a device for detecting volatile substances characterized in that it comprises a containment box having at least one inlet opening for the introduction of a gas flow, preferably chromatographic degree air, one or more outlet openings of the gas flow, at least one analysis opening, one or more detection sensors arranged within the containment box, and at least one probe, insertable within the containment box through the at least one analysis opening, so that, when the probe is treated beforehand by a sample of a substance to be examined and it is inserted within the containment box, the gas flow uniformly carries the volatile substances from the sample to the one or more sensors.

According to the invention, the port of the analysis opening is smaller than the sum of the ports of the one or more outlet openings so that the insertion or the extraction of the probe from the analysis opening does not change the flow of the gas that reaches the sensors.

Still the ratio between the port of the analysis opening and the sum of the ports of the one or more outlet openings is lower than and/or equal to 0.01.

Furthermore, the containment box has a bottom base where the inlet opening is made, and a top base opposed with respect to the bottom base, where the one or more outlet openings and the analysis opening for the introduction of the probe are made, the number of the outlet openings being equal to the number of the one or more sensors.

Advantageously, according to the invention, the detection device comprises a body arranged within the containment box, the body being provided with a through channel in which the first end communicates with the analysis opening and the second end communicates with the inside of the containment box.

According to the invention the containment box can be a removable body.

According to the invention one or more sensors can be installed on the internal lateral surface of the containment box.

Furthermore, according to the invention, the containment body has a cylindrical shape and the body has a substantially spheroidal shape, the body radially providing on its surface a plurality of channels, in a number corresponding to the number of sensors, the channels ensuring a sufficient and even partialization of the gas, and thus of the sample, toward each one of the sensors.

Advantageously, according to the invention the body can have one of the following features: it is made of an insulating material, so that when the probe is inserted within the channel, the sample of a substance to be examined does not evaporate while the probe is inserted through the channel; or it is made in such way that the through channel has a first portion made up of an insulating material, so that the sample of a substance to be examined does not evaporate while the probe is inserted in the part of the through channel of the first portion. The second portion of the body can be made up of a conducting material so that while the probe is inserted through the part of the through channel of the second portion, the sample of a substance to be examined is modified to the internal temperature of the containment box.

According to the invention the device can comprise flow distribution means arranged in correspondence of at least one inlet opening, the flow distribution is suitable to distribute the gas flow through the one or more sensors, the flow distribution comprises a porous separator, preferably made of glass, arranged to delimitate a diffusion chamber of the gas in correspondence of the inlet opening, with respect to a measuring and vaporization chamber, wherein the volatile substances from the sample evaporate and are carried by the gas flow through channels of the central body. The sample is sent toward the sensors.

According to the invention the device can comprise a means for controlling the internal temperature of the containment box. This control preferably comprises a first thermoresistor installed within the diffusion chamber and a second thermoresistor installed within the measuring and vaporization chamber.

Advantageously, according to the invention the substance to be examined is a liquid, preferably urine and/or serum and/or plasma and/or saliva and/or any other biological liquid.

It is further object of the present invention a detection apparatus is characterized in that it comprises at least one detection and measurement device as defined above. The means for supplying the gas flow, comprising a gas cylinder, connected with the inlet opening by a conduit; means for adjusting the temperature of the gas out-flowing from the means for supplying the gas flow; at least one device for reducing the pressure of the gas; at least one flowmeter for adjusting the gas; and a control unit provided with a liquid crystal display and interaction members, the control unit being connected with the means for supplying the gas flow, with the sensors, with the first and second thermoresistor, with the means for adjusting the temperature, with at least one device for reducing the pressure and with the flowmeter, the control unit being suitable to detect the temperature of the gas, to compare the same with the temperature of the diffusion chamber and of the measuring and vaporization chamber, so as to adjust the temperatures by the means for adjusting the temperature and the thermoresistors, to detect the measures of the sensors, and to show the outputs on the display.

It is also an object of the present invention is a method for detecting volatile substances by means of the device for detecting volatile substances, comprising the following steps: providing a probe; treating, for example by immersion, the end of the probe in a sample of a substance to be examined, preferably a liquid sample, such as urine; and introducing the probe within the detection device as defined in the above through the analysis opening.

BRIEF DESCRIPTION OF DRAWINGS

The present invention will be now described for illustrative, but not limitative purposes, according to its preferred embodiments, with particular reference to the enclosed drawings, wherein:

FIG. 1 shows a lateral section view of a device for detecting and measuring volatile substances according to the present invention;

FIG. 2 shows a plan section of a device for detecting and measuring volatile substances according to FIG. 1:

FIG. 5 is a table wherein showing samples of substances subjected to testing and relevant amounts.

Similar parts will be indicated by the same references in the different views.

DETAILED DESCRIPTION

Figure 3:
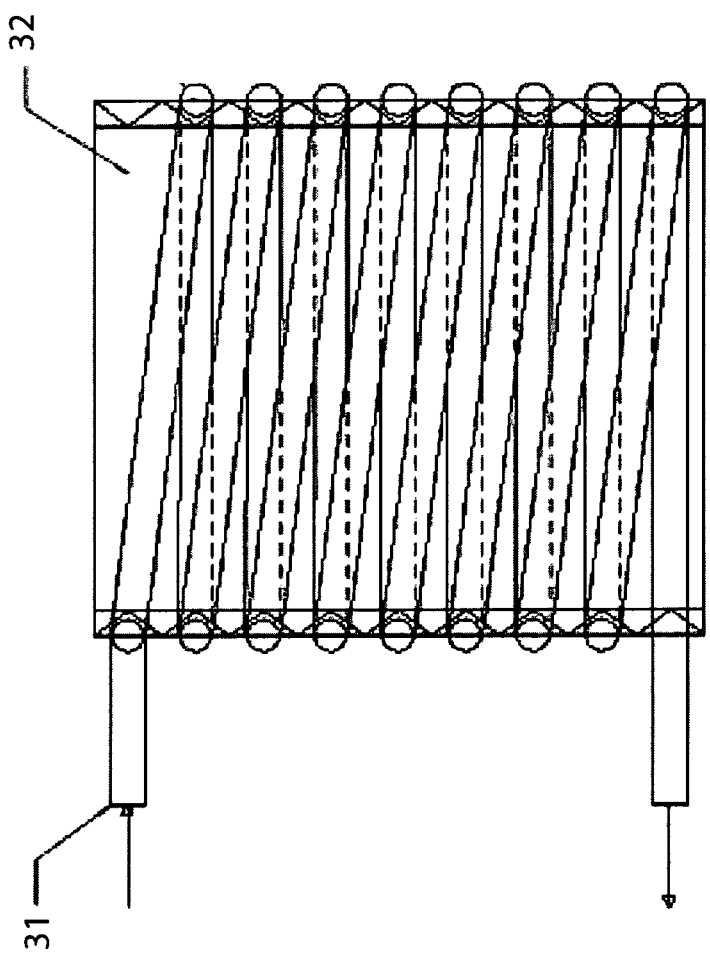
FIG. 3 shows a heating resistance for a device for detecting and measuring volatile substances according to the present invention.

Making reference to FIGS. 1 and 2, a device is observed for detecting volatile substances according to the invention. Device 1 comprises containment box 20, within which there are a plurality of detection sensors that, in the present embodiment, are six sensors and are indicated by reference numbers 51, 52, 53, 54, 55 and 56. A carrier gas is sent to sensors 51-56, as better described in the following. Structure of containment box 20 realizes a diffusion chamber D and a vaporization and measurement chamber M. Volatile parts of a previously introduced sample of a substance to be subjected to analyses and evaporated within containment box 20, are transported by the flow of the carrier gas to sensors 51-56.

Examining in greater detail device 1, it is observed that, in the present embodiment, containment box 20 has a cylindrical shape and a bottom base 21, an upper base 22 and a lateral wall 23.

An opening 30 is obtained on bottom base 21, in order to introduce the carrier gas within diffusion chamber D, under pressure by a conduit 31. Entering carrier gas flow it heated up before, so that it has the same inner temperature of containment box 20.

FIG. 3 shows an embodiment of the heating means of device 1, comprising a heating band-like resistance 32, on which conduit 31 is wound like a coil.

The gas employed is preferably chromatographic grade gas, having the required purity in order to prevent introduction of substances to sensors 51-56 which would jeopardize the measurement results. Furthermore, gas flow is adjusted by a pressure reducer and monitored by a flowmeter.

Thus, carrier gas enters within containment box at a temperature avoiding every condensation that could occur in case the gas carrier temperature is lower than a temperature which could cause evaporation of volatile parts within the sample. In fact, possible condensation randomly varies concentration of evaporated substances within carrier gas, thus making unreliable analyses.

In view of the high sensitivity of the measurement system suitable to analyze micro amounts, a remarkable stability of carrier gas flow is required which does not create particular problems under static conditions but can cause limitations during introduction. Thus, device 1 provides a particular geometry.

Coming back to FIGS. 1 and 2, it is observed that six outlet openings for carrier gas are obtained on upper base 22, two of which are shown in the section view, respectively indicated by reference numbers 41 and 42. The openings are circularly provided and at the same distance from each other in the present embodiment.

The number of sensors 51-56 is the same number of carrier gas outlet openings; moreover, the latter are provided in correspondence of sensors 51-56, so as to ease outlet of carrier gas flow from containment box 20. Sensors 51-56 can be of different types and different numbers, or they can all be the same.

Furthermore, among most versatile sensors, it is possible to use conductivity variation sensors, piezoelectric sensors, quart microbalance (QCM), surface acoustic wave sensors (SAW), MOSFET sensors, and thermo conductivity sensors.

Device 1 also provides gas diffusion means 60, defining diffusion chamber D. The gas diffusion chamber 60 is suitable to diffuse gas entering through opening 30 within vaporization and measurement chamber M, to send it toward sensors 51-56.

Particularly, the gas diffusion means 60 comprises of a porous septum 61, preferably comprised of glass, provided with a plurality of through holes (not shown in the figures). Porous septum 61 is spaced with respect to opening 30 by a ring 62. Porous septum 61 and ring 62 define diffusion chamber D. Porous septum 61 ensures a capillary diffusion of gas flow, and through channels realized within the central body 73, it is ensured right partialization of flow toward every sensor. The channels are vertical milling, with a depth of about 10 mm, realized on lateral wall of body 73. In case six sensors are provided, the channels have a 60° distance between axes. Distance between axis angle of 360° is divided by the number of sensors.

Furthermore, a first thermoresistor (not shown in the figure) is provided within diffusion chamber D for controlling temperature within containment box 20. Furthermore, a Teflon® disk 63 is provided on the porous septum, the function of which will be better described in the following.

In order to make a detection, it is necessary to place a substance to be subjected to examination within the box, so that it can be taken from gas flow and sent toward sensors 51-56. To this end, an analysis opening 71 is obtained on the upper base 22 of containment box 20, communicating with the vaporization and measurement chamber M by a through channel 72 of a body 73, preferably a removable body, provided within containment box 20. The body 73 has a substantially spherical shape. Dimensions and shape of body 73 are particularly suitable to ensure a partialization of gas flow (transporting extracted substances) uniform on sensors 51-56. Each sensor 51-56 is thus interested by the same volume of sample. By the above solutions it is possible to obtain specific response signals that are solely a function of the substance amount, without any interference due to the amount concerning every single sensor 51-56 employed. In other words, the amount of extracted substances from sample concerning every single sensor is exactly the same amount for each of them, thus preventing a response signal depending on the amount and on the quality of the substance to be subjected to examination.

It must be taken into consideration that the number of sensors can be varied. Generally speaking, no structural modification is necessary with a number of sensors between 1 and 12. Furthermore, sensors 51-56 can be fixed to the inner surface of wall 23 of containment box 20 or, preferably, to body 73. In the latter case, said body being removable, replacing the same, partializing the carrier gas flow toward single sensors, the number of sensors 51-56 can be easily modified. Obviously, type and number of sensors to be used only depends on substances to be subjected to examination and to quantify.

Through channel 72 is substantially provided in correspondence of the symmetry axis. Body 73 of the present embodiment is comprised of insulating material, in order to prevent that, while the substance to be subjected to examination is introduced through channel 72 within measurement and vaporization chamber M, the substance to be subjected to examination evaporates before arriving at the same chamber.

To position the sample of the substance to be subjected to examination, it is provided the use of sampling probe 80, that can be realised as a rod, a closed capillary or the like, in any case having an elongated shape, and comprised of a chemically inert material, resistant to temperature and having such a section to be able to pass through the analyses opening 71 and channel 72.

Sampling probe 80 is at least partially submerged (typically about 5 mm) within substance to be subjected to analysis, to be "wet" by the sample to be subjected to examination. The same result can be obtained by rubbing, or by any other method permitting "wetting," a portion of sampling probe 80. Sampling probe 80 so treated is introduced within diffusion chamber D, within which, under the effect of temperature, volatile portion of the sample quickly passes to gaseous state and carrier gas flow sends it toward sensors 51-56.

When sampling probe 80 is inserted within channel 72 through analysis opening 71, the "wet" end reaches porous septum 61. Teflon® disk 63 is suitable to prevent sampling probe 80 from hitting porous septum 61.

Carrier gas, through diffusion chamber D, reaches glass porous septum 61 and is diffused within measurement cell M. Volatile substances contained within the "wet" portion (end) of the probe, evaporate and gas carries them toward sensors 51-56. Then, gas flow exits from vaporization and measurement chamber M through the outlet openings.

Gas flow, through porous septum 61, thanks to the shape of body 73, creates suitable flow paths within body 73, within vaporization and measurement of chamber M, and it is radially diffused toward every sensor 51-56. Six outlet openings and Teflon® disk 63, centrally provided on porous septum 61, create preferred paths through which gas, and thus volatile substances, flow.

Flow resistance due to analysis opening 71, through which sampling probe 80 is inserted or withdrawn, has a much higher value of flow resistance caused by outlet openings 41 or 42 of the gas flow, so that introduction, or withdrawal, of sampling probe 80 from through channel 72 does not create appreciable variations of carrier gas flow balance toward sensors 51-56. In a preferred embodiment, ratio between port of analysis opening 71 and sum of ports of the outlet openings is in the order to $1/100$ (0.01).

The solution ensures flow stability necessary to the repetitivity of responses from employed sensors that would unavoidably vary physical conditions (temperature, pressure and flow) of gas passing through them.

Figure 4:
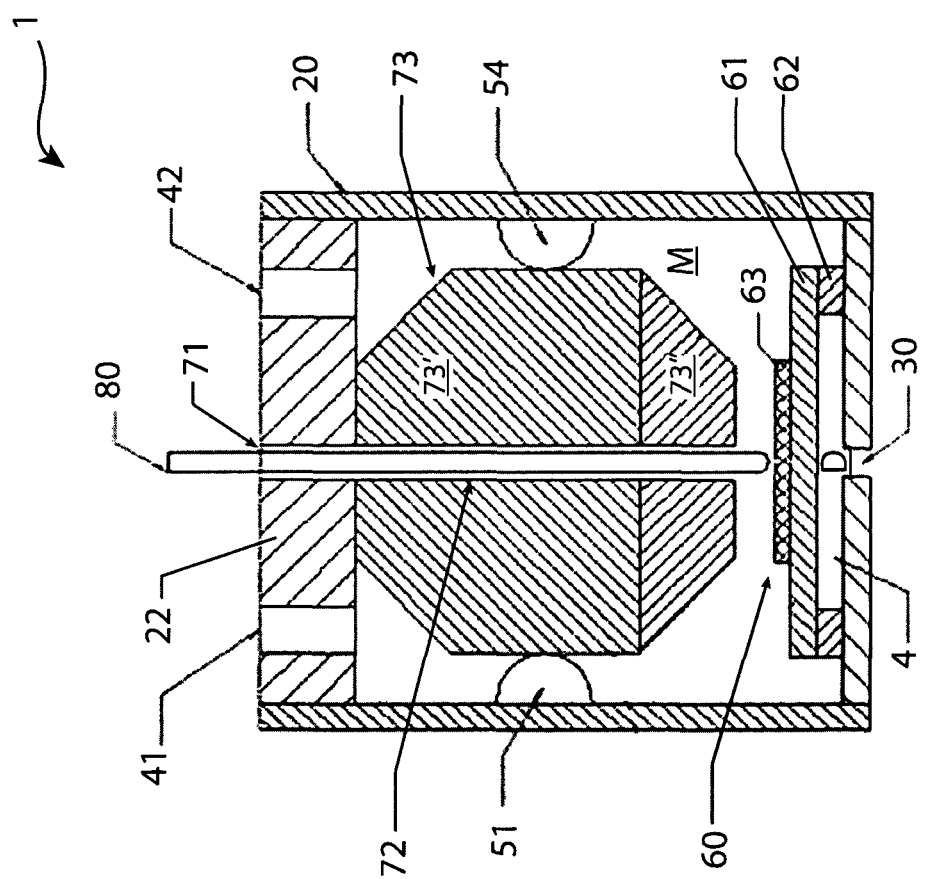
FIG. 4 shows a second embodiment of detecting and measuring volatile substances according to the present invention.

FIG. 4 shows a further embodiment of the device according to the invention, wherein body 73 is so realised that a first portion 73" is comprised of insulating material, so that channel 72 of the portion has walls comprised of the insulating material; and a second portion 73" is comprised of thermally conductive material, as walls of the relevant portion of channel 72.

Thus, when probe 80 with the sample to be subjected to analysis is introduced within containment box 20, first insulated portion prevents the sample from evaporating, while the second final portion brings the sample to the temperature of vaporization and measurement chamber M.

Preferably, a second PT100 thermoresistor (not shown in the figures) is installed in vaporization and measurement chamber M, to detect temperature in order to permit a control and comparison with the temperature of diffusion chamber D.

Usually, sampling probe 80 can have different shape and dimensions, on the basis of the sample to be subjected to analysis. Anyway, maximum diameter must be 4 mm. Moreover, probes for solid samples and probes for liquid samples can be individuated.

Liquid sample probes are realised by a support rod, comprised of material resistant to temperature and chemically inert materials (glass, ceramics, stainless steel, etc.). The probes provide an end curve, which is "wet" by immersion within liquid, in order to take the sample to be subjected to analysis.

Solid sample probes are comprised of chemically inert materials, resisting to temperature and mechanically not deformable. Usually, they have a cylindrical shape, with a pointed tip, easing introduction within solid samples. Their use provides an introduction of the sample for the following withdrawal. Volatile parts, if present within sample, remain on the probe, which are injected within device 1, introducing the probe within a suitable opening.

Solid sample probes can also be used for sampling volatile substances present in a gaseous atmosphere, e.g. in human breath. In order to realise the above, it is necessary such an equipment which, by a Peltier battery system, refrigerates the probe up to the temperature of −8° C. (adjustable value). The refrigerated probe, if brought into contact with a gaseous atmosphere, "catches" volatile substances, freeing them and, when introduced within device 1, releases the same within the gas, by which they are sent to sensors 51, 52, 53, 54, 55 and 56.

Device 1 can even operate in a suitable apparatus (not shown in the figures), essentially providing a gas flow generation unit comprising a cylinder connected with conduct 31.

The apparatus also comprises of a control unit provided with a control panel with a liquid crystal display and interaction members such as a keyboard.

The control unit is connected to sensors 51-56, with the thermoresistors installed within diffusion chamber D and within vaporization and measurement chamber M, to pressure reducer and to flowmeter. By this solution, diffusion chamber D and vaporization and measurement chamber M are at the same temperature. This permits preventing the hottest or coldest spots along the evaporated substances path toward sensors 51-56 make concentration differences within the gas, with consequent unreliable responses. In fact, in case points when different temperature are present within device 1, they would not permit a proper partialization of the sample toward sensors 51-56 and, taking into consideration micro amounts introduced and vaporised, responses would not be proportional to gas concentration, but rather would randomly vary.

Temperature can be set at a maximum value by sensors' 51-56 maximum exercise temperature. Anyway, it is advisable to choose the highest possible temperature, to be sure that all volatile parts of the sample pass to the gaseous phase.

Adjustment of temperature is of the proportional type, permitting reaching a precision of 0.1° C. order.

The adjustment stability is essential for sensor 51-56 response, both in a static phase and during analysis. Actual value can be continuously monitored by the display on the apparatus control panel.

FIGS. 5-8 show some experimental data, with homovanillic acid and vanilmandelic acid as samples to be subjected to analysis, at different urine concentrations of healthy people. Sampling, and injection of the sample, have been carried out as described in the above, i.e. wetting a probe end 80 and inserting the same within through channel 72.

Figure 6:
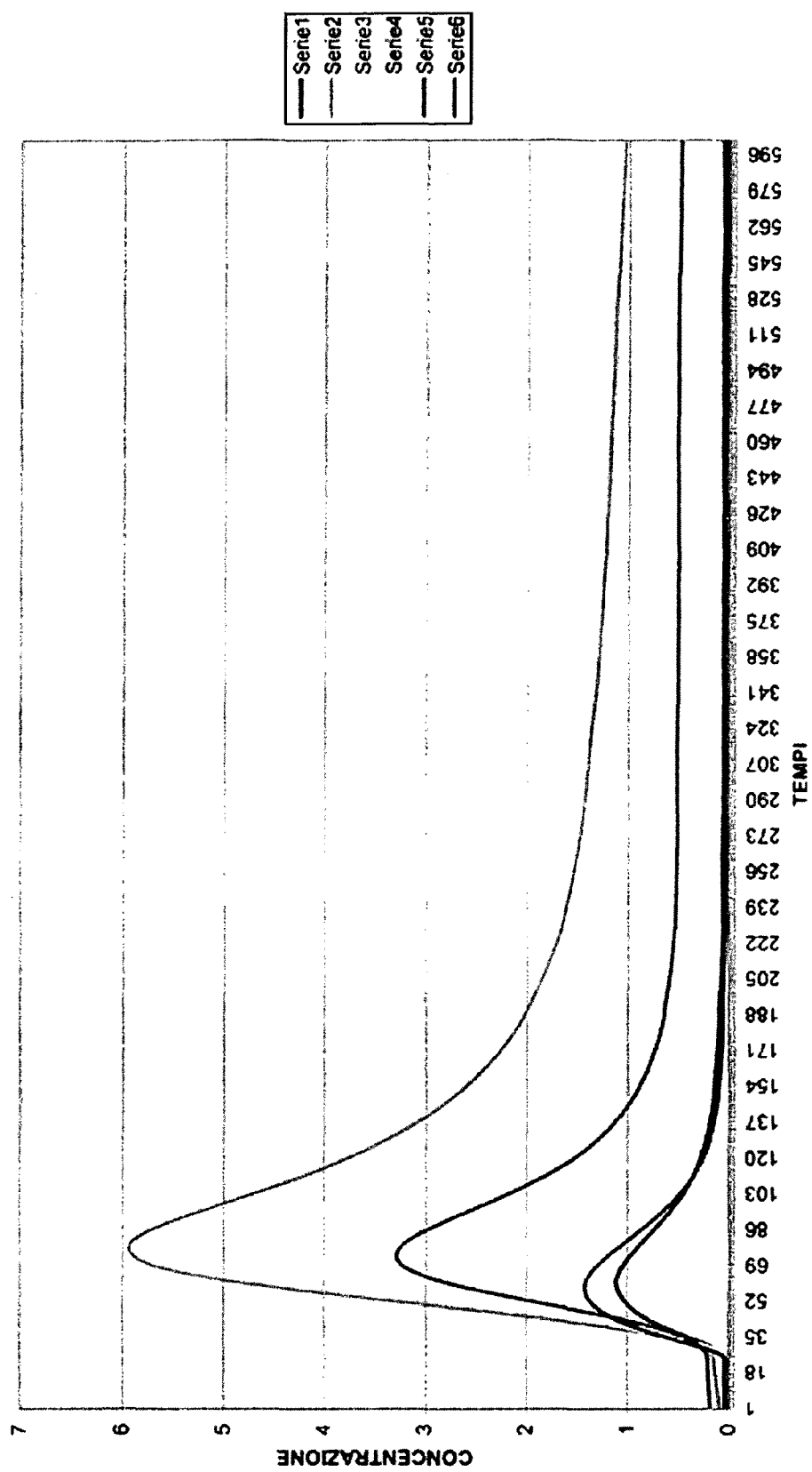
FIGS. 6-8 show curves indicating, for example, responses of sensors to homovanillic and vanilmandelic acid obtained by the device according to the invention.
Figure 7:
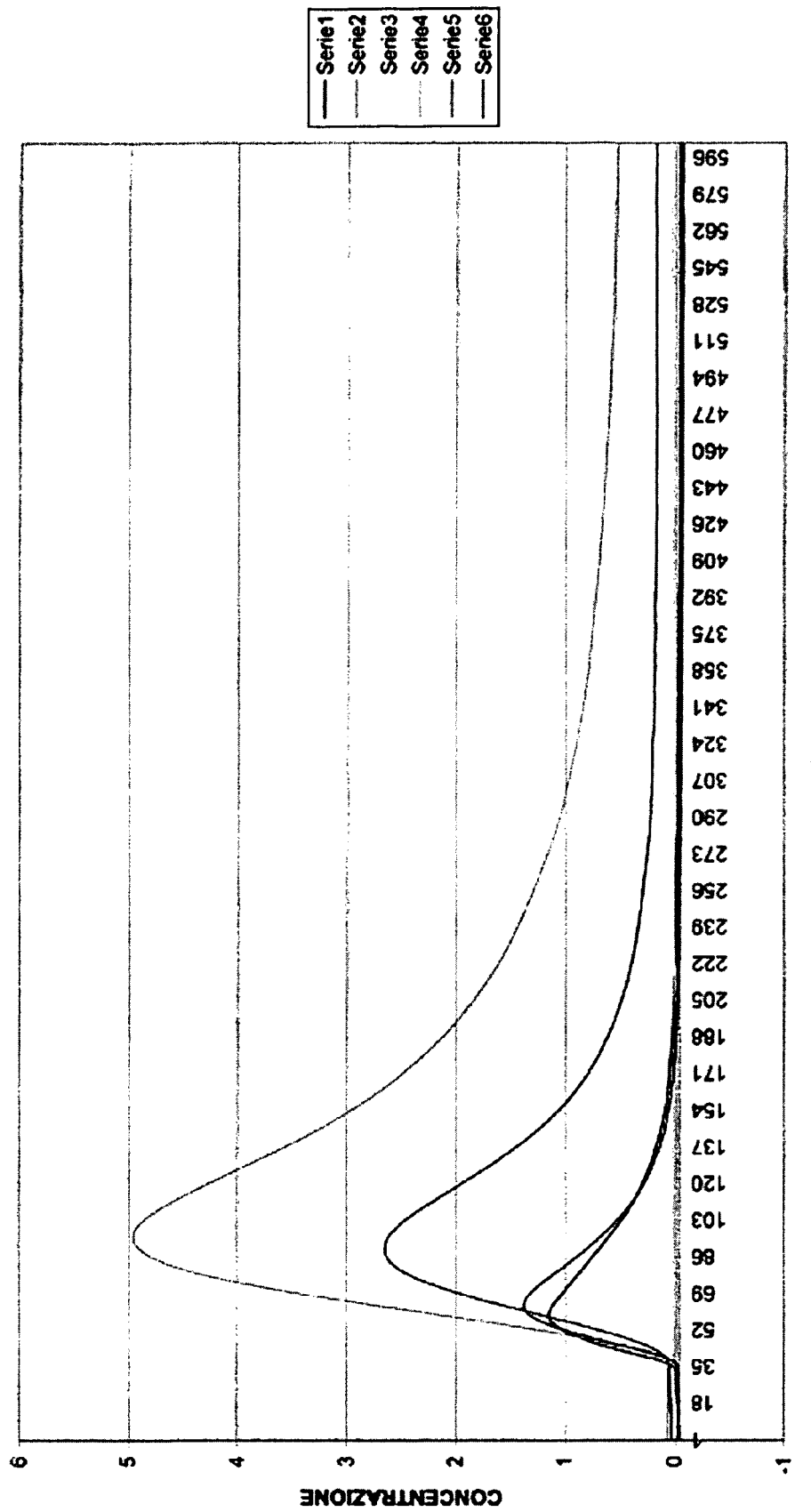
Figure 8:
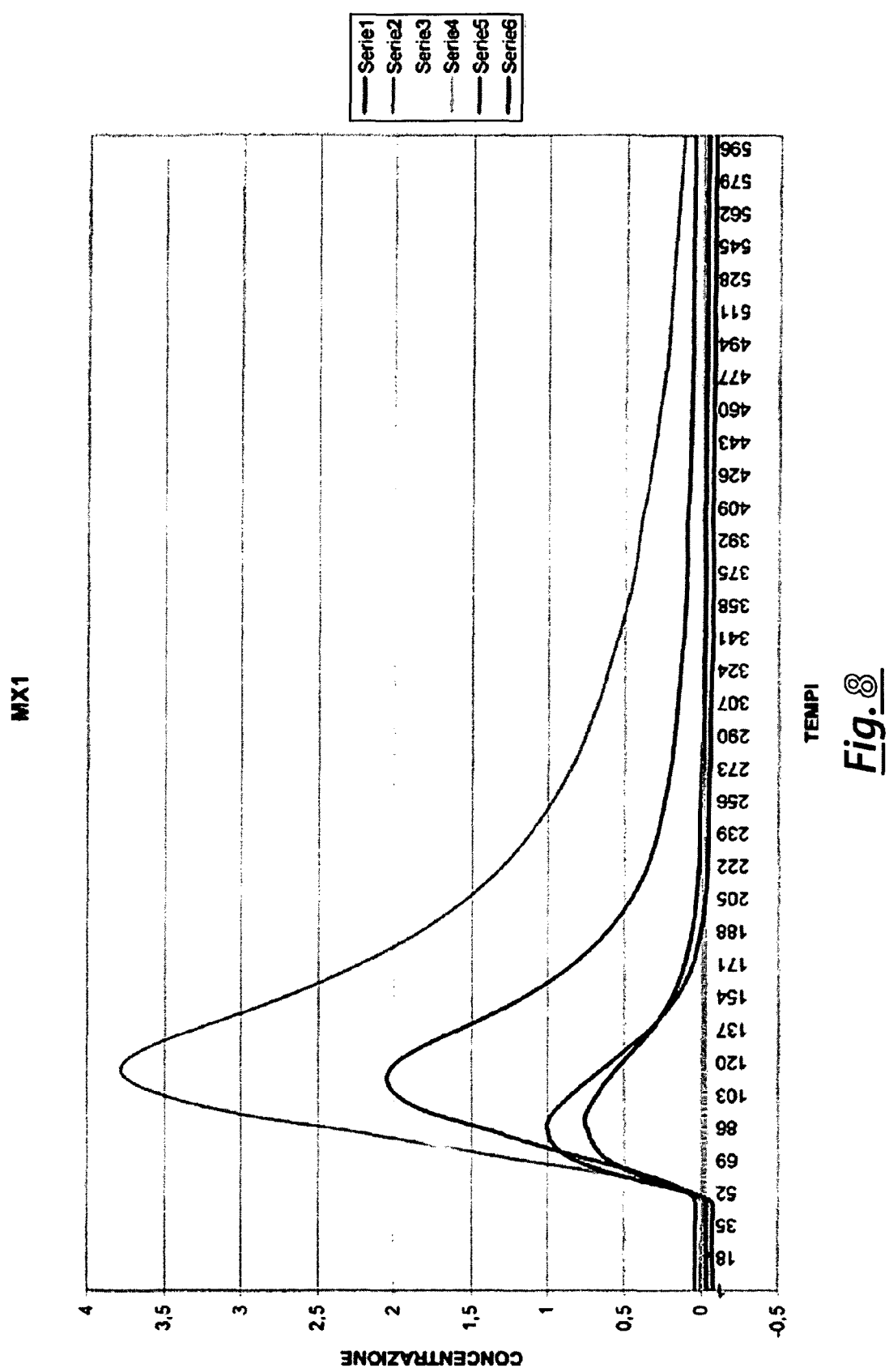

FIG. 5 shows a table of the solutions subjected to the test, while FIGS. 6-8 show graphs of responses of homovanillic acid and vanilmandelic acid while time passes, obtained by the device according to the invention. Time is shown in abscissa and response to concentration of components of analyses substance is shown in ordinate. Lack of response from sensor 56 is noted from above the graph. This is due to a minimal, almost null, response from the employed sensor for substances under examination. An advantage of the present invention is that detection device can detect small amounts of samples (order of micro liters) and it permits a very quick measurement. Furthermore, it is easy to use at low costs.

A further advantage of the invention is that the device can be used in all apparatuses designed to analyse micro amounts of volatile substances in liquid but also solid samples, and thus it can be applied to biomedical, food, chemical, environmental, etc fields.

The present invention has been described for illustrative, but not limitative purposes, according to its preferred embodiments, but it is to be understood that variations and/or modifications can be introduced by those skilled in the art without departing from the relevant scope, as defined in the enclosed claims.

The invention claimed is:

1. A device for measurement of volatile substances, comprising
    a containment box, having at least one inlet opening for introduction of a gas flow, one or more outlet openings of said gas flow and at least one analysis opening,
    one or more detection sensors arranged within said containment box, and
    at least one probe, insertable within said containment box through said at least one analysis opening,
    wherein a dimension of a port of said analysis opening is smaller than a dimension of a sum of ports of said one or more outlet openings, so that insertion or extraction of said probe from said analysis opening does not change the flow of said gas that reaches said sensors,
    said device further comprising a body arranged within said containment box, said body being provided with a through channel that has a first end communicating with said analysis opening and a second end communicating with the interior of said containment box,
    wherein said body is radially provided on its surface with one or more channels, in a number corresponding to a number of said one or more detection sensors, said channels being located on a lateral wall of said body and being suitable for partialization of gas flow toward each detection sensor, so that, when said probe is treated beforehand by a sample of a substance to be examined and is inserted within said containment box, said gas flow uniformly carries the volatile substances from said sample to said one or more detection sensors.

2. The device according to claim 1, wherein a ratio between the dimension of said port of said analysis opening and the dimension of the sum of the ports of said one or more outlet openings is lower than or equal to 0.01.

3. The device according to claim 1, wherein said containment box has a bottom base, where said at least one inlet opening is made, and a top base, opposed with respect to said bottom base, where said one or more outlet openings and said analysis opening for the introduction of said probe are made, the number of said outlet openings being equal to the number of said one or more detection sensors.

4. The device according to claim 1, wherein said containment box body is a removable body.

5. The device according to claim 1, wherein said one or more detection sensors are located on an internal lateral surface of said containment box.

6. The device according to claim 1, wherein said containment box is a cylindrical shape and said body is a substantially spheroidal shape.

7. The device according to claim 1, wherein said body:
    i) is made of an insulating material, so that said sample to be examined does not evaporate while said probe is inserted through said channel; or
    ii) is configured such that said through channel has a) a first portion made of an insulating material, so that said sample to be examined does not evaporate while said probe is inserted through said first portion, and b) a second portion made of conducting material, so that, while said probe is inserted through said second portion, said sample to be examined is modified to a preset internal temperature of said containment box.

8. The device according to claim 1, said device further comprising a flow distribution arrangement arranged in correspondence with said at least one inlet opening, said flow distribution arrangement being suitable to distribute said gas flow through said one or more detection sensors,
    said flow distribution arrangement comprising a porous separator, arranged to delimitate a diffusion chamber of said gas in correspondence of said inlet opening with respect to a measuring and vaporization chamber, wherein the volatile substances from said sample evaporate and are carried by said gas flow, by said channels of said central body, when said sample is sent toward said sensors.

9. The device according to claim 8, said device further comprising a control arrangement for controlling an internal temperature of said containment box.

10. The device according to claim 1, wherein said substance to be examined is a liquid or a vapor.

11. The device according to claim 1, wherein said substance to be examined is a solid.

12. The device according to claim 1, said device further comprising a Peltier battery system for cooling said at least one probe before sampling a volatile substance and inserting the same through said at least one analysis opening.

13. A detection and measurement apparatus comprising:
   at least one device for measurement of volatile substances according to claim 8;
   a supplying arrangement for supplying said gas flow, comprising a gas cylinder, connected with said inlet opening by a conduit;
   an adjusting arrangement for adjusting temperature of said gas outflowing from said supplying arrangement;
   at least one device for reducing the pressure of said gas;
   at least one flowmeter for adjusting said gas; and
   a control unit provided with a liquid crystal display and interaction members, said control unit being connected with said supplying arrangement, with said one or more detection sensors, with said adjusting arrangement, with said at least one device for reducing the pressure and with said flowmeter, said control unit being suitable to detect the temperature of said gas, to compare said temperature with a temperature of said diffusion chamber and of said measuring and vaporization chamber, so as to adjust said temperatures by said adjusting arrangement, to detect measures of said one or more detection sensors, and to show the outputs on said display.

14. A method for detecting volatile substances through the device for the measurement of volatile substances according to claim 1, comprising the steps of:
   providing a probe;
   treating, an end of said probe in a sample of a substance to be examined; and
   introducing said probe within said device through said analysis opening of said device.

15. The method of claim 14, wherein the sample is a liquid sample.

16. The method of claim 15, wherein the liquid sample is urine.

17. The device of claim 1, wherein the gas is chromatographic grade air.

18. The device of claim 8, wherein the porous separator is made of glass.

19. The device according to claim 9, wherein the control arrangement comprises a first thermoresistor installed within said diffusion chamber and a second thermoresistor installed within said measuring and evaporation chamber.

20. The method of claim 14, wherein the step of treating occurs by immersion.

* * * * *